United States Patent
Long et al.

(10) Patent No.: US 9,315,909 B2
(45) Date of Patent: Apr. 19, 2016

(54) MOLECULAR MOLYBDENUM PERSULFIDE AND RELATED CATALYSTS FOR GENERATING HYDROGEN FROM WATER

(75) Inventors: Jeffrey R. Long, Oakland, CA (US); Christopher J. Chang, Berkeley, CA (US); Hemamala I. Karunadasa, Palo Alto, CA (US); Marcin Majda, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 946 days.

(21) Appl. No.: 13/403,573

(22) Filed: Feb. 23, 2012

(65) Prior Publication Data

US 2012/0217169 A1    Aug. 30, 2012

Related U.S. Application Data

(60) Provisional application No. 61/446,400, filed on Feb. 24, 2011.

(51) Int. Cl.
| | | |
|---|---|---|
| *C07F 15/02* | (2006.01) | |
| *C07F 1/08* | (2006.01) | |
| *C25B 1/04* | (2006.01) | |
| *C07F 7/28* | (2006.01) | |
| *C07F 13/00* | (2006.01) | |
| *C07F 9/00* | (2006.01) | |
| *C07F 15/06* | (2006.01) | |
| *C07F 11/00* | (2006.01) | |
| *C25B 3/04* | (2006.01) | |
| *B01J 31/18* | (2006.01) | |
| *B01J 31/22* | (2006.01) | |

(52) U.S. Cl.
CPC ............... *C25B 3/04* (2013.01); *B01J 31/1815* (2013.01); *B01J 31/226* (2013.01); *C07F 11/005* (2013.01); *B01J 2231/62* (2013.01); *B01J 2531/0241* (2013.01); *B01J 2531/16* (2013.01); *B01J 2531/46* (2013.01); *B01J 2531/56* (2013.01); *B01J 2531/62* (2013.01); *B01J 2531/64* (2013.01); *B01J 2531/66* (2013.01); *B01J 2531/72* (2013.01); *B01J 2531/842* (2013.01); *B01J 2531/845* (2013.01); *B01J 2531/847* (2013.01)

(58) Field of Classification Search
None
See application file for complete search history.

*Primary Examiner* — Yun Qian
(74) *Attorney, Agent, or Firm* — Lawrence Berkeley National Laboratory (57) ABSTRACT

New metal persulfido compositions of matter are described. In one embodiment the metal is molybdenum and the metal persulfido complex mimics the structure and function of the triangular active edge site fragments of $MoS_2$, a material that is the current industry standard for petroleum hydro desulfurization, as well as a promising low-cost alternative to platinum for electrocatalytic hydrogen production. This molecular $[(PY5W_2)MoS_2]^{x+}$ containing catalyst is capable of generating hydrogen from acidic-buffered water or even seawater at very low overpotentials at a turnover frequency rate in excess of 500 moles $H_2$ per mole catalyst per second, with a turnover number (over a 20 hour period) of at least 19,000,000 moles $H_2$ per mole of catalyst.

6 Claims, 11 Drawing Sheets

MOLECULAR MOLYBDENUM PERSULFIDE AND RELATED CATALYSTS FOR GENERATING HYDROGEN FROM WATER

CROSS REFERENCE TO RELATED APPLICATIONS

This application claims priority to U.S. Provisional Application Ser. No. 61/446,400 filed Feb. 24, 2011, which application is incorporated herein by reference as if fully set forth in their entirety.

This application relates to PCT Patent Application Serial No. PCT/US2010/048405, filed Sep. 10, 2010, entitled Molecular Metal-Oxo Catalysts for Generating Hydrogen from Water, which application claims priority to U.S. Provisional Patent Application 61/249,877, filed Oct. 8, 2009, both of which applications are incorporated herein by reference as if fully set forth in their entirety.

STATEMENT OF GOVERNMENTAL SUPPORT

The invention described and claimed herein was made in part utilizing funds supplied by the U.S. Department of Energy under Contract No. DE-AC02-050411231 between the U.S. Department of Energy and the Regents of the University of California for the management and operation of the Lawrence Berkeley National Laboratory. The government has certain rights in this invention.

BACKGROUND OF THE INVENTION

1. Field of the Invention

This invention relates generally to a new composition of matter, and more specifically to new high oxidation state metal persulfido complex that can be used for generating hydrogen from water, in one embodiment the high oxidation state metal being molybdenum.

2. Brief Description of the Related Art

Owing to issues of climate change and accelerating global energy demands, the search for viable carbon-neutral sources of renewable energy is amongst the foremost challenges in science today. One such alternative is hydrogen, which can potentially be used as a clean replacement for fossil fuels in many applications, including transportation in cars, buses, trucks, trains, and airplanes. It can further be used in fuel cells for powering mobile devices such as lap-top computers and cell phones, as well as for meeting power requirements in buildings and industry. Many industries also use hydrogen as a reactant. One example is the Haber-Bosch process that produces ammonia, which currently relies on steam reforming of natural gas or liquefied petroleum for the production of hydrogen. This is expensive, environmentally unsustainable (based on finite resources of fossil fuel and produces carbon dioxide and hydrogen sulfide, two major atmospheric pollutants) and necessitates removal of sulfur which deactivates the catalyst used for ammonia production. Hydrogen is also used as a reducing agent for metal ores, for the production of hydrochloric acid and as a hydrogenating agent for unsaturated fats and oils.

In this context, where hydrogen has emerged as an attractive candidate for a clean, sustainable fuel as well as a precursor to many essential compounds, an intense interest in creating artificial systems that utilize earth-abundant catalysts for efficient hydrogen production from water has developed. A major quest of this renewable energy research is the search for efficient catalysts for the production of hydrogen from water which rely on cheap, earth-abundant elements.

Hydrogenase enzymes possessing earth-abundant iron and/or nickel cofactors have been found to catalytically evolve $H_2$ from neutral aqueous solutions at its thermodynamic potential, with turnover frequencies of 100-10,000 mols $H_2$/mol catalyst per second. However, the large size and relative instability of these enzymes under aerobic, ambient conditions has led to the search for well-defined molecular complexes outside the biological milieu that can produce $H_2$ from water. Although many examples of air- and moisture-sensitive synthetic iron-sulfur clusters have provided insight into hydrogenase structure and reactivity, they catalyze proton reduction from acids in organic solvents at fairly negative potentials of $-0.9$ to $-1.8$ V vs. the SHE (Standard Hydrogen Electrode). Metal complexes that evolve $H_2$ at more positive potentials still require organic acids, additives, and/or solvents. As such, the creation of earth-abundant molecular systems that produce $H_2$ from water with high catalytic activity and stability remains a significant basic scientific challenge.

Water electrolysis has also been achieved through the use of precious metal catalysts (e.g. platinum, palladium) and purified water, as well as at elevated temperatures, all of which makes the process expensive. In a search for lower cost alternatives, in related case PCT US2010/048405, a low cost alternative to the precious metal catalysts is described. More particularly, these low cost metal complexes are salts wherein the cation comprises a PY5 metal-oxo ion. (As used herein, PY stands for pyridine and PY5 indicates the presence of five pyridyl rings). The positively charged cations of those compositions were described by the general formula $[(PY5W_2)MO]^{2+}$, wherein $PY5W_2$ is $(NC_5XYZ)(NC_5H_4)_4C_2W_2$, and M a high oxidation state metal. In one disclosed embodiment, the metal was molybdenum (Mo), which in terms of cost is about 74 times lower than the cost of platinum, the current preferred catalyst for hydrogen production. In other disclosed embodiments, W, X, Y, and Z of the general formula were described as being selected from the group comprising H, R, a halide, $CF_3$, or $SiR_3$, where R is an alkyl or aryl group. The substitutions at the X, Y, and Z positions were further disclosed as being either the same or different. Finally the group attached to the quaternary carbon at the W position was described as either being hydrogen, methyl, a higher alkyl or aryl group or any one of the halogens F, Cl, Br and I, $CF_3$ or $SiR_3$. The accompanying negative ions (i.e. the counter anion) for these metal-oxo salt compositions said to be any one of a number of anions, including a halide such as $Cl^-$, $I^-$, or $PF_6^-$, $CF_3SO_3^-$, and so forth. The exact composition of the anion was not found to be significant, as it was not found to play a significant role in the water to hydrogen reaction. These pentapyridine ligand complexes are semi rigid, and in their salt form easily dissolve in water.

These organo metal-oxo complexes catalytically generated hydrogen from water at neutral pH. In one embodiment, the organo metal-oxo complex was an organo molybdenum-oxo complex, which in experiments successfully generated hydrogen for at least 3 days, with a turnover frequency (TOF) of at least 1.47 million mol $H_2$/mol catalyst per hour (i.e., 408 mol $H_2$/mol catalyst per second) and a turnover number (TON) of 105 million mol $H_2$/mol catalyst. Moreover, this same molecular system was used to evolve $H_2$ from seawater, the earth's most abundant source of protons.

The discovery of a molecular metal-oxo catalysts, and more particularly molybdenum-oxo catalysts for generating hydrogen from water without use of additional acids and/or organic co-solvents established a new chemical paradigm for creating reduction catalysts that are highly active and robust in aqueous media. Importantly, that system employed an inexpensive, earth-abundant metal to achieve catalytic $H_2$ evolution from neutral buffered water or even seawater, maintaining long-term activity with TOF values in excess of 400 or more mol $H_2$/mol catalyst per second and TON values of 105 million mols $H_2$/mol catalyst. An overpotential of between –0.6 V to –1.0 V at the cathode lead to an efficiency of 67%-55% respectively for the cell, assuming that the rest of the cell was operated at ideal efficiencies.

Notwithstanding the success of the MO based catalyst, and more particularly the MoO based catalyst, there remains the need for a low cost and efficient catalyst for generating hydrogen gas from water, which is stable, low cost, and can produce hydrogen at even lower over-potentials than that currently realized with MO.

SUMMARY OF THE INVENTION

Here reported is a new composition of matter wherein the cation of the composition can be represented by the general formula $[(PY5W_2)MS_2]^{x+}$, this composition having the ability to catalyze the generation of hydrogen from water. In one aspect of the invention, the metal is Mo. Also reported is a method for the synthesis of a molecular analog of the $MoS_2$ edge structure, the side-on bound $Mo^{IV}$-persulfido complex of this invention, which composition has the ability to catalyze the generation of hydrogen from water with turnover frequencies (TOFs) reaching approximately 500 moles $H_2$ per mole catalyst per second and turnover numbers (TONs) reaching (in one experiment run for 20 hours) over 19,000,000 moles $H_2$ per mole of catalyst. Results demonstrate that discrete molecules resembling the catalytically active fragments of inorganic solids can mimic the structure and reactivity of these extended materials, and can further operate at rates within range of hydrogenase enzymes. Also described herein as one embodiment of the invention is a species of the persulfido $[(PY5W_2)MoS_2]^{2+}$ complex where W in this embodiment is methyl, the $MoS_2$ containing salt used as a catalyst to generate hydrogen from water at low pH, especially at pHs significantly lower than 7. In one embodiment, the pH can be lower than 5, in another embodiment it can be lower than 4, and in still yet another embodiment it can be around 3. This new molecule represents a rare species in molybdenum coordination chemistry and a discrete molecular analog of the triangular $MoS_2$ edge sites of molybdenite.

Figure 1:
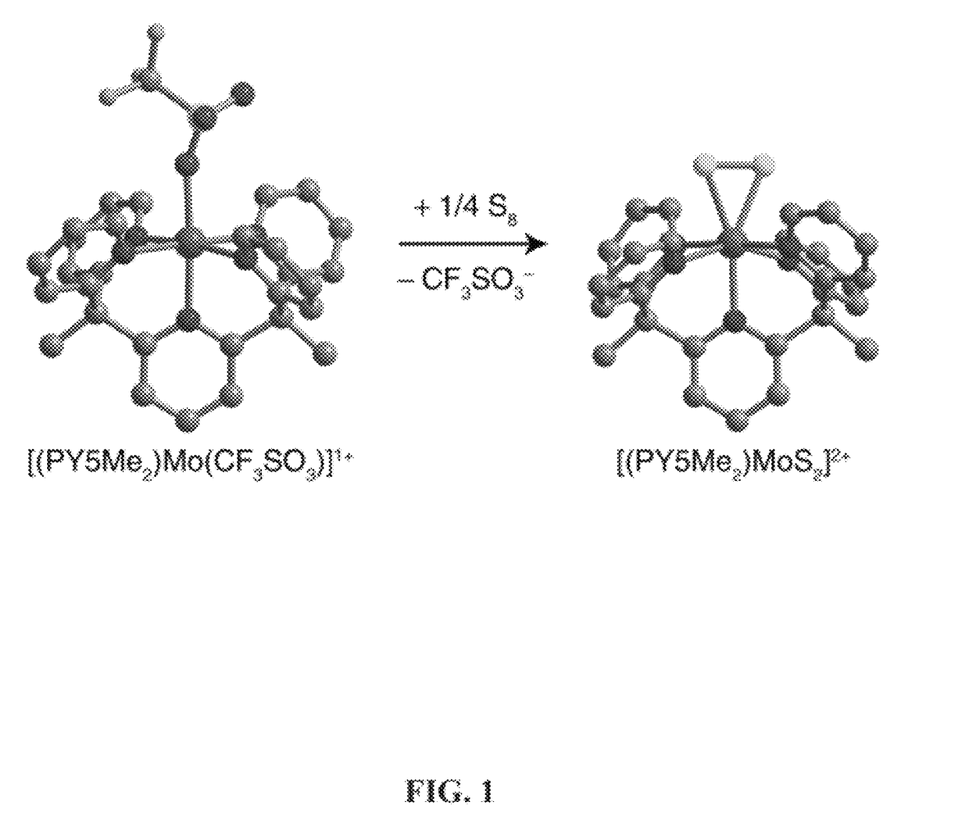
FIG. 1 is a three dimensional representation of an embodiment of the invention showing the reaction pathway for obtaining the final product $[(PY5Me_2)MoS_2]^{2+}$, by reacting the precursor $[(PY5Me)Mo(CF_3SO_3)]^{1+}$ with $S_8$. The green, yellow, light blue, red, blue and gray spheres represent Mo, S, F, O, N, and C atoms, respectively. H atoms have been omitted for clarity.

Molybdenite or molybdenum disulfide ($MoS_2$), the earliest form of molybdenum to be identified from ores, is one of the most widely used catalysts in industry today as the standard for hydro desulfurization (HDS) of petroleum (Prins, V. H. J. De Beer, G. A. Somorjai, *Catal. Rev.-Sci. Eng.* 31, 1 (1989). In its nanoparticulate form, it has further been demonstrated as a promising and inexpensive alternative to platinum for the electrochemical generation of hydrogen from water (T. F. Jaramillo et al., *Science* 317, 100 (2007). Like many inorganic solids, the catalytic activity of $MoS_2$ is localized to rare edge sites, whereas the bulk material is relatively inert (G. A. Somorjai, M. A. Van Hove, *Prog. Surf. Sci.* 30, 201 (1989); S. T. Ceyer, *Annu. Rev. Phys. Chem.* 39, 479 (1988); G. Ertl, *Angew. Chem., Int. Ed. Engl.* 29, 1219 (1990). Recent theoretical and experimental studies on solid $MoS_2$ have proposed the formation of disulfide linkages or triangular $MoS_2$ units decorating the catalytically-active edges of the layered structure (B. Hinnemann et al., *J. Am. Chem. Soc.* 127, 5308 (2005); J. V. Lauritsen et al., *J. Catal.* 221, 510 (2004); J. C. Duchet, E. M. van Oers, V. H. J. de Beer, R. Prins, *J. Catal.* 80, 386 (1983). It is this triangular $MoS_2$ unit which forms part of the $PY5Me_2$ ligand complex which provides the catalytic activity of the composition. Synthesis have been achieved by treatment of the $Mo^{II}$ precursor $[(PY5Me_2)Mo(CF_3SO_3)]^{1+}$ with $S_8$ at room temperature which results in the $Mo^{IV}$ persulfide complex $[(PY5Me_2)MoS_2]^{2+}$ of an embodiment of the invention at 74% yield (See FIG. 1).

BRIEF DESCRIPTION OF THE DRAWINGS

The foregoing aspects and others will be readily appreciated by the skilled artisan from the following description of illustrative embodiments when read in conjunction with the accompanying drawings. In hereinafter describing the organo metal complexes of the invention, the shorthand —$MoS_2$, and —MoO will from time to time respectively be used to represent the cations $[(PY5W_2)MoS_2]^{2+}$, and $[(PY5W_2)MoO)]^{2+}$.

DETAILED DESCRIPTION

Recent studies have suggested the formation of disulfide linkages or triangular $MoS_2$ units which decorate the edges of MoS$_2$ bulk materials are responsible for the catalytic activity of these materials, with the bulk of the material thus being relatively inert. By way of one embodiment of this invention, it has been possible to create a discrete molecular molybdenum persulfide complex that mimics the triangular MoS$_2$ active edge sites of molybdenite, and yet provides high activity at low pH for the generation of hydrogen from water.

Figure 2:
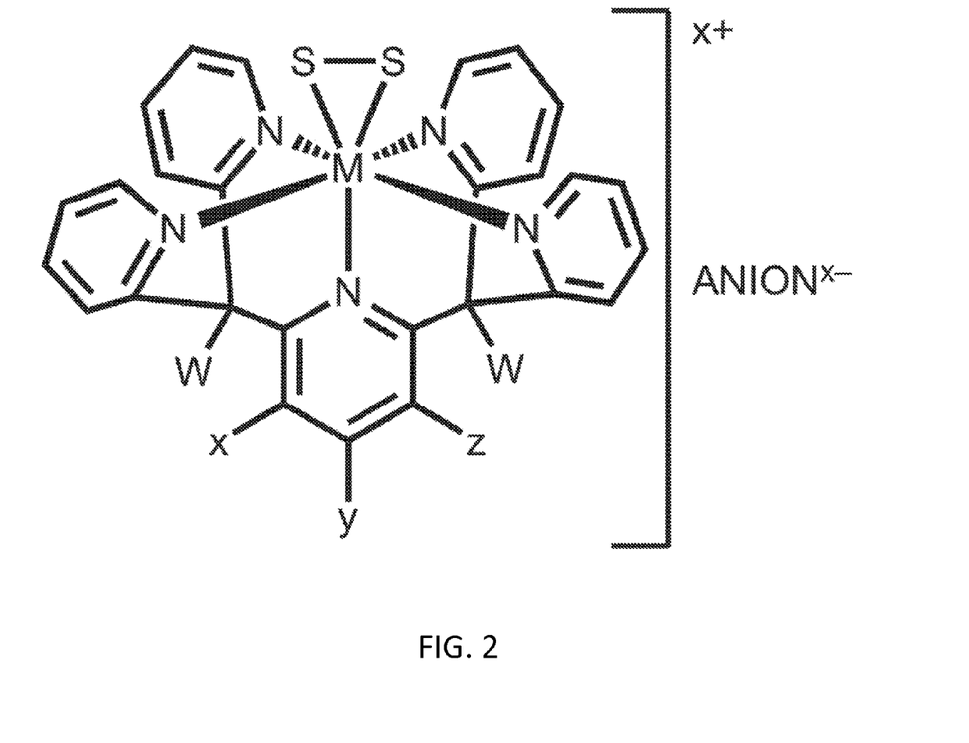
FIG. 2 is a two dimensional schematic of an Mo-persulfido complex according to one aspect of the invention, where W, X, Y, and Z can be H, R, a halide, $CR_3$, $SiR_3$, and the like, where R is an alkyl or aryl group, and the valance states $x^+$ and $x^-$ of the ions are integers, where in one embodiment both x+ and x– are 2.

As with the MO complex described in the related PCT case, the metal persulfide compositions of this invention are similarly represented by the general formula [(PY5W$_2$)MS$_2$]$^{2+}$ (see FIG. 2), where PY stands for pyridine and PY5 indicates the presence of five pyridyl rings. The PY5W$_2$ moiety of the composition can be further expressed by the formula (NC$_5$XYZ)(NC$_5$H$_4$)$_4$C$_2$W$_2$, where W, X, Y, and Z are selected from the group comprising H, R, a halide, CF$_3$, or SiR$_3$, where R is an alkyl or aryl group The substitutions at the X, Y, and Z positions may be the same or different. M is a high oxidation state metal such as Mo, Ti, V, Cr, Mn, Fe, Co, Ni, Cu and Tungsten. In all of these cases, the listed metals are significantly cheaper than the platinum and palladium based catalysts of the prior art, with Mo, Fe and Cu being the cheapest. Finally the group attached to the quaternary carbon at the W position can be either hydrogen, methyl, a higher alkyl or aryl group or any one of the halogens F, Cl, Br and I, CF$_3$ or SiR$_3$. The accompanying negative ions (i.e. the counter anion) for these metal-oxo salt compositions could be any one of a number of anions, including a halide such as Cl$^-$, I$^-$, or PF$_6^-$, CF$_3$SO$_3^-$, and so forth.

In the discussion that follows, the composition tested was [(PY5Me$_2$)MoS$_2$](CF$_3$SO$_3$)$_2$. It is to be appreciated that the negative anion need not necessarily be limited to CF$_3$SO$_3^-$, but can be selected from any number of anions, including Cl$^-$, I$^-$, PF6$^-$, and so forth. The exact nature of the negative ion is not critical as it does not play a significant role in the water to hydrogen reaction. Likewise, while the following discussions focus on Mo, the other low cost metals previously listed such as Cr, Tungsten, etc. could be used in place of Mo so long as the resulting metal complexes are catalytically active at low overpotentials.

General Methods and Materials for the Synthesis of [(PY5Me$_2$)MoS$_2$]$^{2+}$

All manipulations were conducted under air and moisture free conditions using standard glove box and Schlenk-line techniques unless noted otherwise. The compound [(PY5Me$_2$)Mo(CF$_3$SO$_3$)](CF$_3$SO$_3$)$_2$ was synthesized as described in H. I. Karundasa, C. J. Chang, J. R. Long, *A Molecular Molybdenum-oxo Catalyst for Generating Hydrogen from Water*, Nature 464, 1329 (2010), Supplementary Information, page 2, formula (4), a copy of which article and Supplementary Information is attached hereto and incorporated herein by reference as if each were fully set forth in their entirety. Sulfur was purified by sublimation. All other reagents were purchased from commercial vendors and used without further purification. Electronic grade Hg (99.9998%), glassy carbon rods (type 1) and platinum gauze were purchased from Alfa Aesar for the electrochemical studies. Acetonitrile (MeCN) and diethylether (Et$_2$O) were dried and degassed using a VAC 103991 solvent system and stored over 3 Å molecular sieves under a nitrogen atmosphere and 1,2-difluorobenzene was distilled over CaH$_2$ and stored under nitrogen. Water was deionized with the Millipore Milli-Q UF Plus system.

To form [(PY5Me$_2$)MoS$_2$](CF$_3$SO$_3$)$_2$, solid, S8 (7.0 mg, 27 μmol) was added to a 10 mL 1,2-difluorobenze solution of [(PY5Me$_2$)Mo(CF$_3$SO$_3$)](CF$_3$SO$_3$) (86 mg, 100 μmol), and the mixture stirred at room temperature for 48 hours. The solution was filtered to afford a brown solid which was washed with 1,2-difluorobenzene until the filtrate was colorless, and then extracted into 10 ml of MeCN. Diffusion of Et$_2$O into the solution over a period of 3 days yielded 67 mg (a 74% yield) of [(PY5Me$_2$)MoS$_2$](CF$_3$SO$_3$)$_2$, presenting as orange needle-shaped crystals. Analysis of this product single-crystal x-ray structure determination is reported at page S2 of our as yet unpublished paper *A Molecular MoS$_2$ Edge site that can Catalytically Produce Hydrogen from Water*, (22 pages), a copy of this unpublished article attached hereto and incorporated herein by reference as if fully set forth in its entirety.

Electrochemical Studies

A nitrogen filled glove box was used to prepare the aqueous solutions of [(PY5Me$_2$)MoS$_2$] (CF3SO3)$_2$. Buffers were degassed by sparging with water saturated nitrogen prior to the addition of [(PY5Me$_2$)MoS$_2$] (CF$_3$SO$_3$)$_2$. In the presence of oxygen, a yellow solution of the compound was observed to form the green compound [(PY5Me$_2$)MoO)](CF$_3$SO$_3$)$_2$. A mercury pool working electrode was utilized owing to its high overpotential of proton reduction, which eliminates any direct contribution from the reduction of water on the electrode at potentials as negative as −1.2V vs. the SHE at pH 3, The mercury pool had a surface area of ~19.6 cm$^2$, and was stirred constantly during the controlled electrolysis experiments. Electrical contact to the mercury pool was achieved through a platinum wire that remained completely immersed in the mercury, thereby avoiding contact with the solution. A 20.5 cm$^2$ platinum gauge (52 mesh, woven from 0.1 mm diameter wire) was utilized as the auxiliary electrode which was separated front the solution in the working electrode compartment by a medium porosity sintered glass frit.

The reference electrode was a commercially available aqueous Ag/AgCl electrode and the potentials are reported with respect to the SHE by adding 0.195 V to the experimentally obtained values (to account for the measured potential difference between the two electrodes, the 0.195V value established long-ago by others to be the potential difference between the two). Here, overpotential equals the applied potential −E(pH), where E(pH) is (−0.059×pH)V. The working electrode compartment contained 10 mL of electrolyte solution which was thoroughly sparged and kept under a blanket of water saturated nitrogen during the experiments. A 0.05 M potassium hydrogen phthalate/hydrochloric acid buffer (KHP buffer) or a 1 M sodium acetate/acetic acid buffer (acetate buffer) at pH 3 was used as the electrolyte. (While both buffers were employed in the various experiments to maintain the pH around 3, the results as reported were without regard to which one was being used in a particular experiment.) The extended electrolyses (>1 hour) was conducted in a larger cell containing 170 mL of 3M pH 3 acetate buffer and 0.5 M NaCl in each compartment using electrodes of the same dimensions as the other studies. The solutions in both compartments were vigorously stirred during electrolysis. Sea water for the studies was obtained from San Francisco Bay at Crissy Field, San Francisco and was passed through a course paper filter prior to use. An iR compensation was employed to correct for the voltage drop between the reference and working electrodes all experiments using the BASi CV-50W potentiostat and software. Cyclic voltammograms were also run, as further described at page S-3 of our non published paper, with crystallographic data likewise reported at pages S-6 to S-8.

Figure 3:
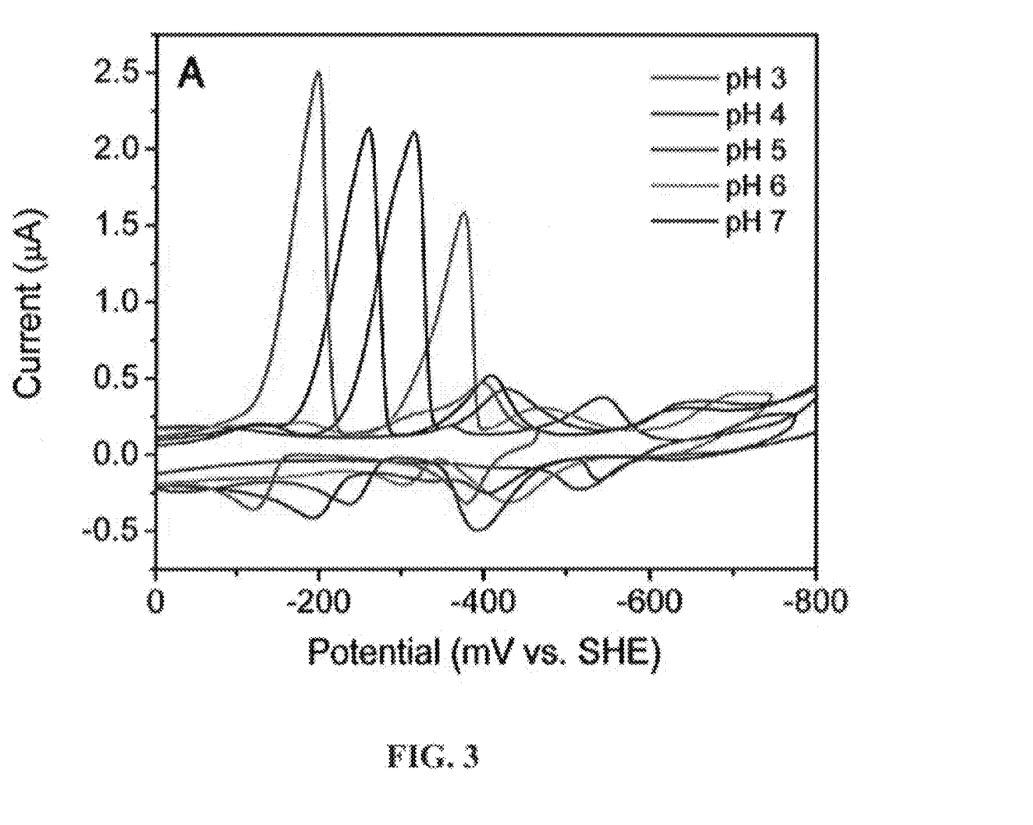
FIG. 3 is a plot of various cyclic voltammograms of $[(PY5Me_2)MoS_2](CF_3SO_3)_2$ in aqueous 005 M KHP buffers at pH ranges of 3-7 on a Hg drop electrode at a scan rate of 1 V/sec.
Figure 4:
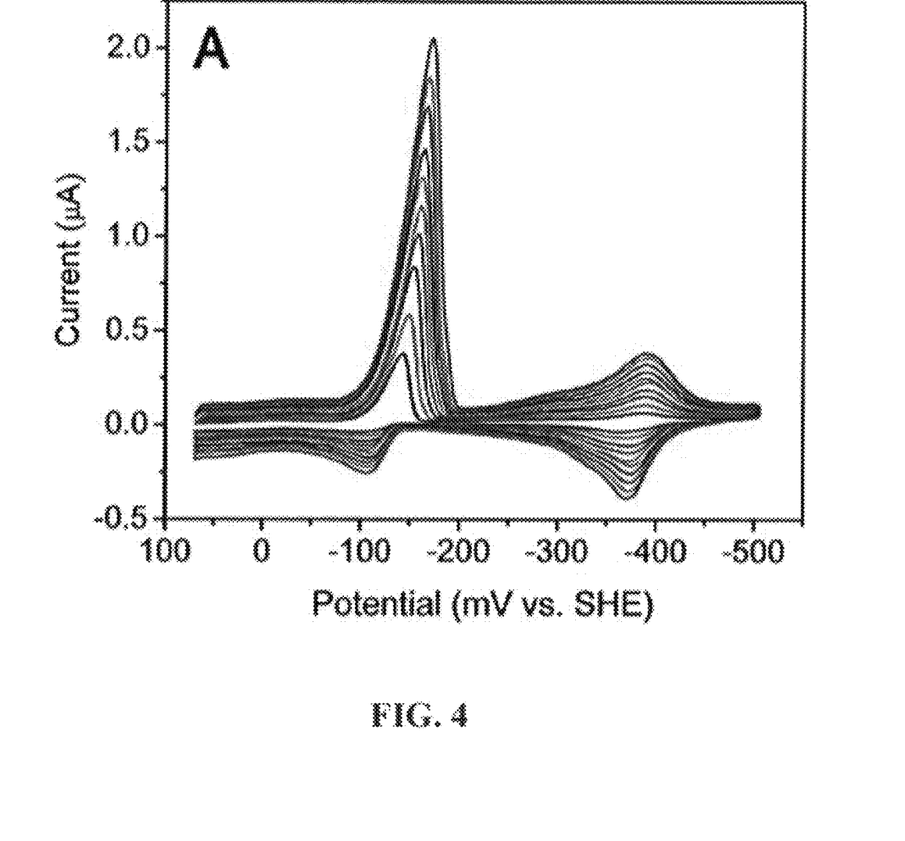
FIG. 4 is a plot of potential (mV vs. SHE) vs. current (μA) showing scan rate dependence of precatalytic waves for a 160 μM solution of $[(PY5Me_2)MoS_2](CF_3SO_3)_2$ in 0.05 M KHP buffer at pH 3, at cyclic voltammogram scan rates ranging from 100-1000 mV/s in 100 mV/s increments on a mercury drop electrode (A~11.6×10⁻³ cm²).
Figure 5:
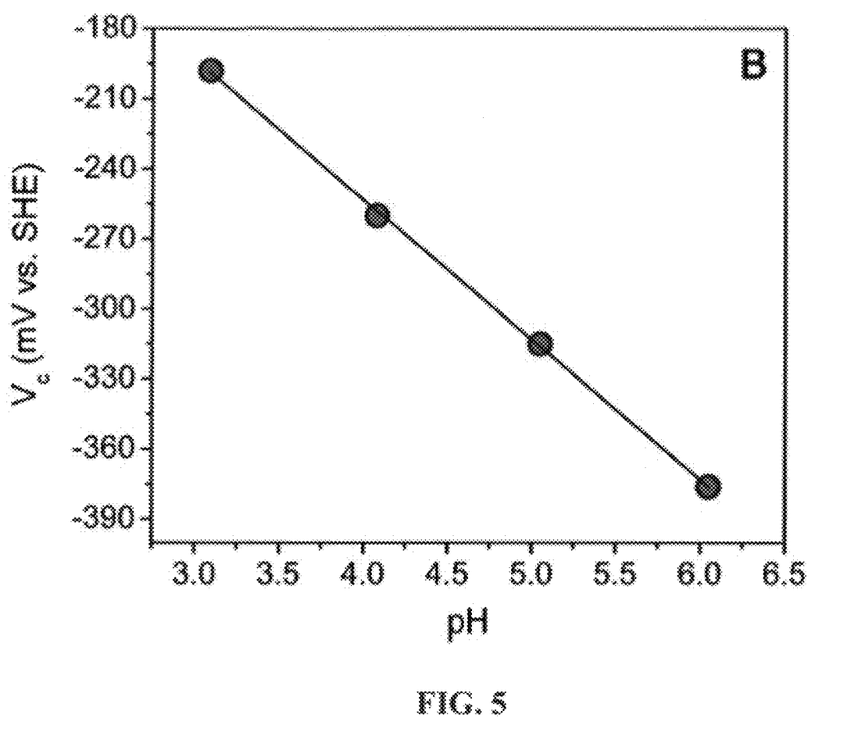
FIG. 5 is a Pourbaix diagram of voltage vs. pH showing the dependence of the peak potential of the first reductive wave on the solution pH. A linear fit gives a slope of 59.8 (±0.8).

These experiments were carried out using a mercury electrode, owing to its low background activity, which eliminates direct water reduction at the electrode until overpotentials are applied which are greater than 1 V (overpotential=applied potential−thermodynamic potential for water reduction at the same pH). A sharp increase in current, indicative of catalytic water reduction, is evident in cyclic voltammograms of [(PY5ME$_2$)MoS$_2$](CF$_3$SO$_3$)$_2$ taken at pH values of 3, 4, 5, 6 and 7, with optimal activity observed at pH 3 (FIG. 3). Subsequent studies were conducted at pH 3 using either potassium hydrogen phthalate or sodium acetate as an aqueous buffer. A cyclic voltammogram measured at a scan rate of 0.5 V/s (See FIG. 4) exhibits a sharp wave corresponding to the first reduction at −0.161 V vs. SHE, followed by a quasi-reversible couple at $E_{1/2}$=−0.381 V preceding the catalytic current. To probe the nature of the first reduction process, we investigated the pH dependence of the peak potential ($V_c$) to construct the Pourbaix diagram depicted in FIG. 5. Here, $V_c$ shows a linear relation with the solution pH with a slope of −59.8(±0.8), which is close to the ideal value of −59 mV corresponding to the association of one proton with the electron transfer process.

Figure 6:
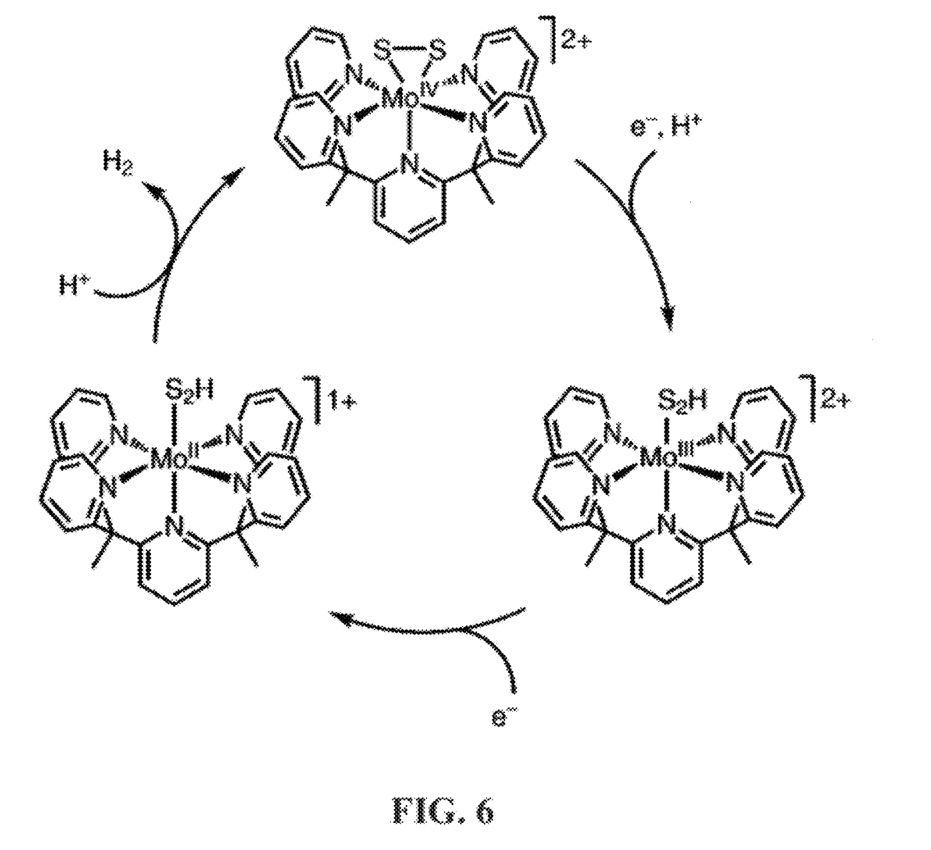
FIG. 6 is an illustration of a possible catalytic cycle for the reduction of protons in water as mediated by $[(PY5Me_2)MoS_2](CF_3SO_3)_2$.
Figure 7:
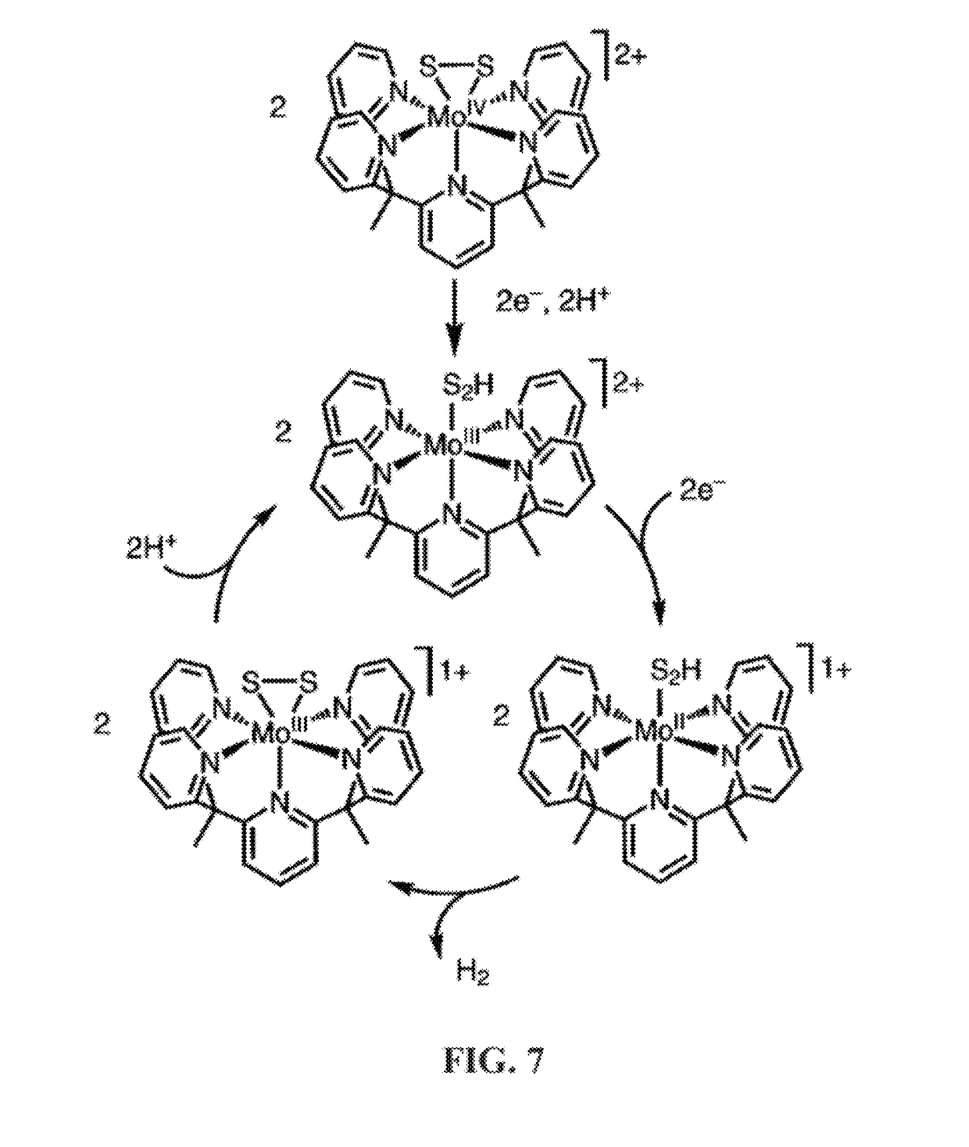
FIG. 7 is an illustration of another possible alternative catalytic pathway for the hydrogen formation reaction.

The observed pH dependence, taken together with the irreversibility of this peak, suggest a geometric distortion of the molecule consistent with the formation of a protonated Mo$^{(III)}$-persulfide complex. Interestingly, formation of an S—H bond is the first step in the proposed pathway for electrocatalytic proton reduction at —MoS$_2$ nanoparticle edge sites. In contrast, the second reductive wave does not show similar pH dependence, leading to the hypothesis that this reduction forms a Mo$^{II}$—SSH species, which, upon subsequent protonation, loses H$_2$ to regenerate the starting complex. A bimolecular pathway where two Mo$^{II}$—SSH complexes come together to evolve H$_2$ and generate a Mo$^{III}$S$_2$ complex is also possible (as illustrated in FIG. 6 and FIG. 7.)

Figure 8:
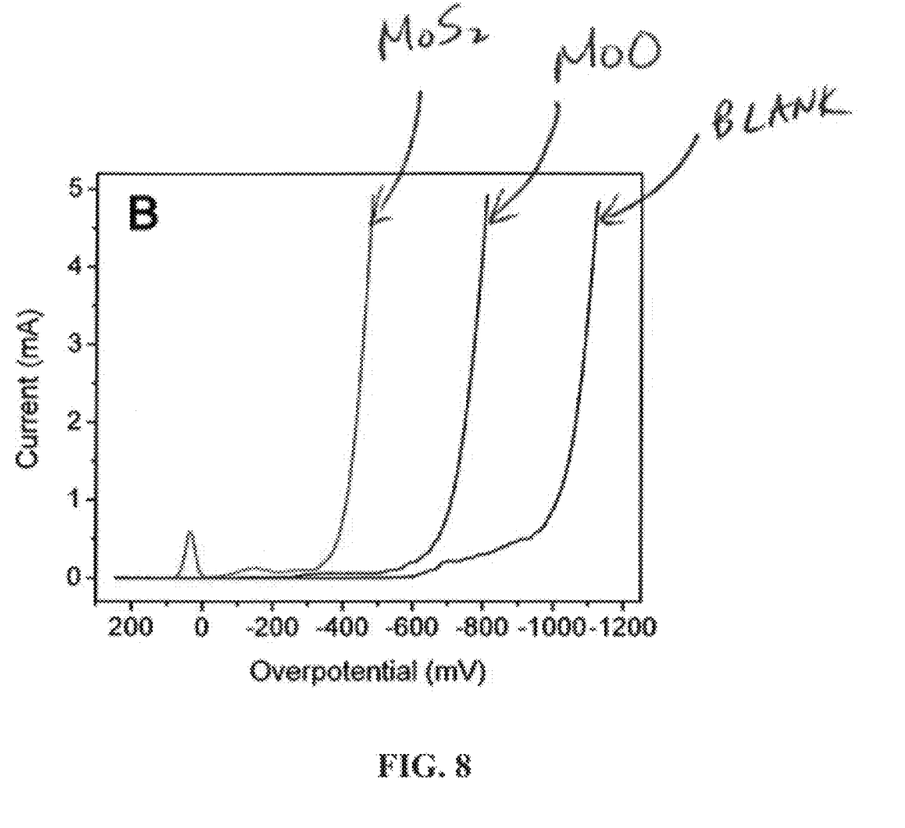
FIG. 8 is a plot of current vs. overpotential comparing a blank (blue line), with 130 μM solutions of $[(PY5Me_2)MoS_2](CF_3SO_3)_2$ (orange line) and $[(PY5Me_2)MoO](CF_3SO_3)_2$ (green line) in aqueous 1 M pH 3 acetate buffer on a mercury pool electrode (A=19.6 cm²) at a scan rate of 100 mV/s.

Controlled potential electrolysis experiments were conducted to assess the rate of hydrogen production at various overpotentials. The cyclic voltammogram of a 130 µM solution of [(PY5Me$_2$)Mo(S$_2$)](CF$_3$SO$_3$)$_2$ at pH 3 shows a catalytic current with an overpotential of ca. −400 mV (FIG. 8). The catalytic performance of [(PY5Me$_2$)MoO]$^{2+}$ was also evaluated at the same pH to establish that [(PY5Me$_2$)Mo(S$_2$)](CF$_3$SO$_3$)$_2$ did not form the molybdenum-oxo complex under aqueous, reducing conditions. As depicted in FIG. 8, [(PY5Me$_2$)MoO]$^{2+}$ shows the onset of a catalytic current at an overpotential of −700 mV under the same conditions. Thus, the persulfide —MoS$_2$ complex shows an improvement of 300 mV in overpotential with respect to the analogous oxo complex for water reduction at pH 3. Identical controlled potential electrolysis measurements were performed without a catalyst to subtract the background activity at each applied potential.

Figure 9:
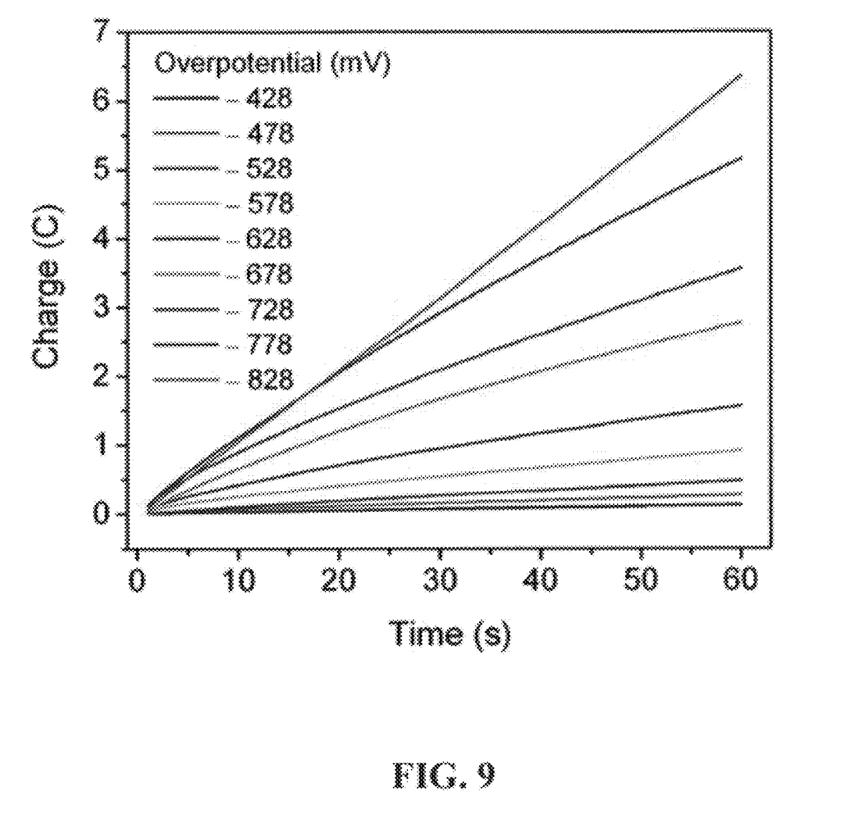
FIG. 9 is a plot of time vs. charge as measured in Coulombs as a further result of various applied overpotentials for a 190 μM solution of $[(PY5Me_2)MoS_2](CF_3SO_3)_2$ in a 0.05 M KHP buffer at pH 3.

FIG. 9 shows the charge (in Coulombs) accumulated over one minute intervals, with applied overpotential increasing from −428 mV until a saturation value of 6.36 C is reached at −828 mV (due to the voltage between the working and auxiliary electrodes overcoming the maximum voltage obtainable by the potentiostat at high current densities). Under these conditions, gas chromatography of the headspace gas confirmed that the catalyst indeed evolved. H$_2$, and the pH change of the buffer indicated that the catalyst performs at close to 100% Faradic efficiency, where every electron is used for the generation of hydrogen. At an overpotential of −828 mV, the observed TOF increases reached a maximum of 280 moles H$_2$ per mole catalyst per second.

Figure 10:
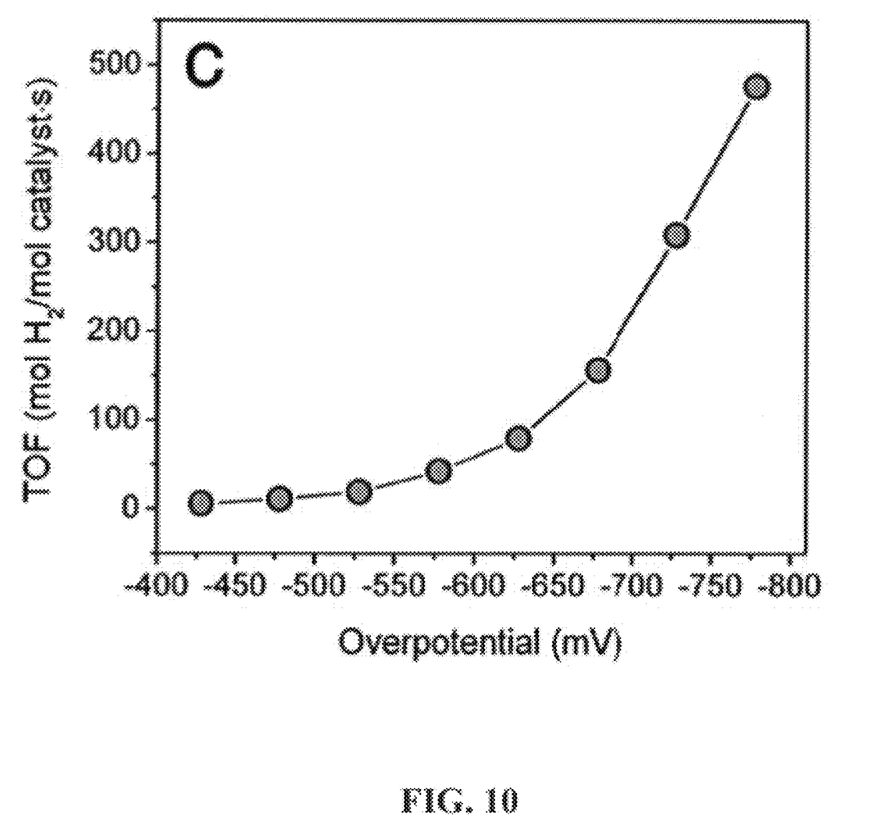
FIG. 10 is a plot of overpotential in mV vs. TOF expressed as mol $H_2$ per mol of catalyst for a 170 μM solution of —$MoS_2$ in seawater maintained at pH 3 with 1 M acetate buffer. The background solvent activity has been subtracted from the data.
Figure 11:
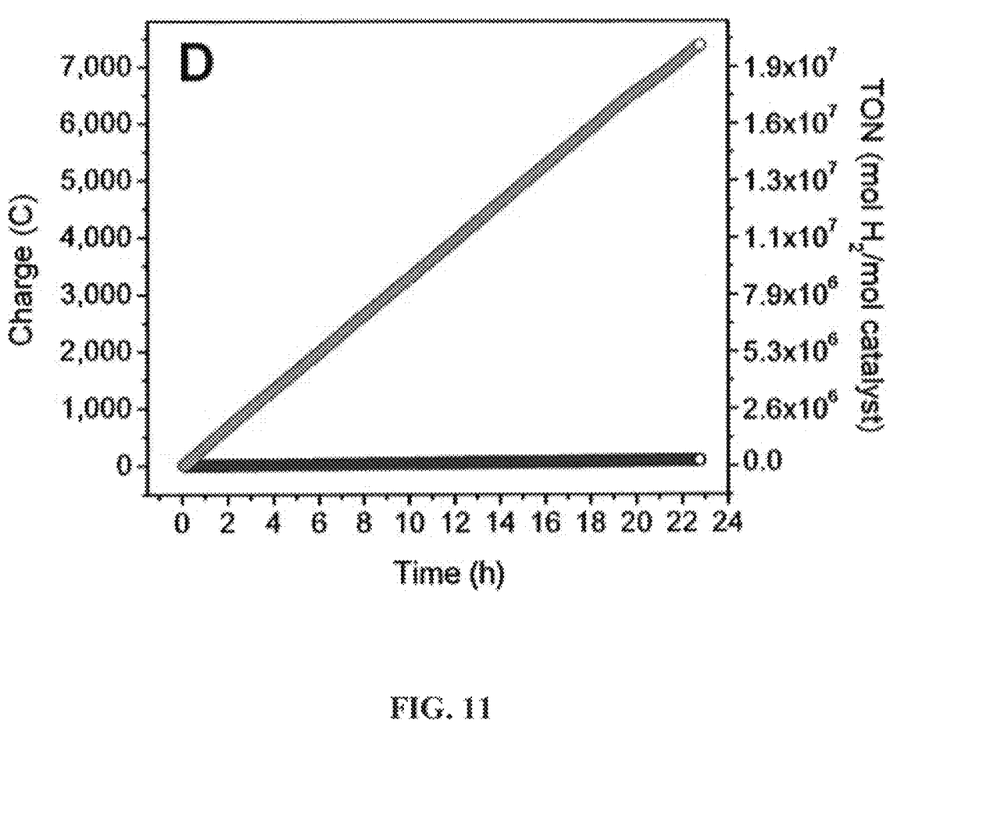
FIG. 11 a plot as a function of time for a 66 μM solution of —$MoS_2$ in 3 M pH 3 acetate buffer, showing charge build-up and turnover number (TON) versus time (orange circles), and data for the electrolyte solution alone (blue circles) with the cell operating at an overpotential of –778 mV, the overpotential equaling the applied potential –E(pH 3).

Also evaluated were the catalytic properties of [(PY5Me$_2$)MoS$_2$](CF$_3$SO$_3$)$_2$ using a sample of California seawater, which was buffered at pH 3 by the addition of acetic acid and sodium-acetate. As shown in FIG. 10, the rate of hydrogen evolution for a given overpotential were similar to the studies conducted in distilled water, but with an even higher optimal TOF of 480 moles H$_2$ per mole catalyst per second at an overpotential of −778 mV. This result highlights the robustness of the catalyst to the impurities found in seawater. To assess the long-term stability of the catalyst, an extended electrolysis was conducted for a period of 20 hours in pH 3 acetate buffer at an overpotential of −778 mV. The total TON reached over 19,000,000 moles H$_2$ per mole catalyst (FIG. 11), showing that the catalyst is stable for long durations in aqueous media with its activity apparently limited only by the capacity of the buffer.

To the best of our knowledge, the catalyst [(PY5Me$_2$)Mo(S$_2$)](CF$_3$SO$_3$)$_2$ exhibits the highest rate and lifetime for hydrogen production by a surface-adsorbed molecular complex in aqueous solution. Remarkably, its TOF is comparable to those of hydrogenase enzymes, nature's optimized hydrogen producing catalysts, which operate at rates between 100 and 10,000 moles H$_2$ per mole enzyme per second. While enzymes operate close to the thermodynamic limit for H$_2$ evolution, these molecules are significantly larger in size and are typically unstable under non-biological settings. Catalyst [(PY5Me$_2$)Mo(S$_2$)](CF$_3$SO$_3$)$_2$ shows much greater stability under ambient conditions and is robust to impurities in water, but does require a greater overpotential. As a further advantage to such molecular catalysts is the feasibility of adjusting the electronic structure at the metal center, and thereby perhaps the required overpotential, through ligand modifications accessible through synthetic chemistry.

In summary, presented herein in one embodiment is a method for the synthesis of a discrete molecular molybdenum persulfide complex that mimics the triangular —MoS$_2$ active edge sites of molybdenite. The high activities for hydrogen evolution from acidic water observed for [(PY5Me$_2$)Mo(S$_2$)](CF$_3$SO$_3$)$_2$ and nanoparticulate —MoS$_2$ suggest a similar structure and mode of action for the site of proton reduction, providing further support for the importance of molybdenum-stabilized sulfur-sulfur contacts at the edges of bulk MoS$_2$.

In another embodiment, other inexpensive metal complexes may be used in place of Mo based metal complexes to prepare hydrogen generating catalysts. This alternative strategy enables one to prepare, characterize, and evaluate molecular analogs of the active components of inorganic solids, which has broad implications for the design and optimization of functional metal sites, not the least of which is control over the density of these units. As earlier noted, and by way of example, recent electronic structure calculations conducted on nanoparticulate MoS$_2$ indicate that only a quarter of the edge sites are used for hydrogen production (B. Hinnemann et al., J. Am. Chem. Soc. 127, 5308 (2005)), and increasing the number of active edge sites per unit volume by progressively smaller nano structures or changing the electronics of the system to increase the enthalpy of hydrogen adsorption has been a major challenge in inorganic materials and nanoscience, which in part is addressed by this invention.

This invention has been described herein in considerable detail to provide those skilled in the art with information relevant to apply the novel principles and to construct and use such specialized components as are required. However, it is to be understood that the invention can be carried out by different equipment, materials and devices, and that various modifications, both as to the equipment and operating procedures, can be accomplished without departing from the scope of the invention itself.

We claim:
1. An organo metal persulfide complex having the following structural formula:

wherein M is a high oxidation state metal selected from the group comprising Mo, Ti, V, Cr, Mn, Fe, Co, Ni, Cu and Tungsten; W, X, Y, and Z are selected from the group comprising hydrogen, methyl, a higher alkyl or aryl group, a halide such as F, Cl, Br, and I, CF3, or SiR3, where substitutions at the X, Y, and Z positions may be optional, and the valance states $x^+$ and $x-$ of the ions are integers.

2. The complex of claim 1 wherein both $x+$ and $x-$ equal 2.
3. The complex of claim 1 wherein the anion is $CF_3SO_3$.
4. The complex of claim 1 wherein the metal is Molybdenum.
5. An organo metal-persulfied complex containg composition of matter comprising:

$[(PY5W_2)MoS_2]^{2+}$ wherein $PY5W_2$ equals $(NC_5XYZ)(NC_5H_4)_4C_2W_2$; and,
W, X, Y, and Z are selected from the group comprising H, methyl, a higher alkyl or aryl group, a halide such as F, Cl, Br, and I, CF3, or SiR3, and where substitutions at the X, Y, and Z positions may be optional.

6. The organo metal-persulfied complex of claim 5 wherein $[(PY5Me_2)Mo(S_2)](CF_3SO_3)_2$.

* * * * *